United States Patent [19]

Klier et al.

[11] Patent Number: 4,480,131
[45] Date of Patent: Oct. 30, 1984

[54] PROCESS FOR SELECTIVE PRODUCTION OF DI- AND TRI-ALKYLAMINES

[75] Inventors: Kamil Klier, Bethlehem; Richard G. Herman, Whitehall; Gamini A. Vedage, Bethlehem, all of Pa.

[73] Assignee: Lehigh University, Bethlehem, Pa.

[21] Appl. No.: 500,037

[22] Filed: Jun. 1, 1983

[51] Int. Cl.$^3$ ............................................. C07C 85/06
[52] U.S. Cl. ..................................................... 564/480
[58] Field of Search ........................................ 564/480

[56] References Cited

U.S. PATENT DOCUMENTS

| | | | |
|---|---|---|---|
| 3,128,311 | 4/1964 | Shirley et al. | 564/480 |
| 4,014,933 | 3/1977 | Boettger et al. | 564/480 X |
| 4,036,883 | 7/1977 | Voges et al. | 564/480 |
| 4,254,060 | 3/1981 | Kimura et al. | 564/480 X |

FOREIGN PATENT DOCUMENTS

| | | | |
|---|---|---|---|
| 1132613 | 9/1982 | Canada | 564/480 |
| 50229 | 4/1982 | European Pat. Off. | 564/480 |

Primary Examiner—Paul F. Shaver
Attorney, Agent, or Firm—Ratner & Prestia

[57] ABSTRACT

A primary alkyl amine and an alcohol of up to 12 carbon atoms are reacted at low temperature (50°–250° C.) over specific catalysts (alkali-treated catalysts generally or binary Cu/ZnO and Pd/SiO$_2$ systems, with or without alkali treatment) to produce, with good selectivity, secondary and tertiary alkylamines of the general formula, $R_1N(R_2)_2$, wherein $R_1$ is a lower alkyl or an aryl group, and $R_2$ is hydrogen or another lower alkyl or aryl group, with at least one of $R_2$'s being an alkyl or aryl group.

9 Claims, No Drawings

PROCESS FOR SELECTIVE PRODUCTION OF DI- AND TRI-ALKYLAMINES

INTRODUCTION

This invention relates to an improved method for the production of alkylamines. More particularly, it is concerned with selectively producing di- and tri-alkylamines by the catalytic reaction of primary amines with alcohols at relatively low temperatures with specific catalysts.

INFORMATION DISCLOSURE STATEMENT PURSUANT TO 37 CFR §1.97

It is reported in the patent literature that amines can be prepared from a reaction of an alcohol with ammonia or from a primary or secondary amine using: (a) metal catalysts; (b) in a strong reducing atmosphere, having three or four catalyst components; (c) at elevated temperatures and pressures; and (d) in the presence of an excess amount of starting amine, so as to insure adequate selectivity in alkylation. (British Patent Specification No. 1,554,516, published Oct. 24, 1978.)

More specifically, known methods for synthesizing higher alkylamines include alkylation of amines or ammonia by alcohols or aldehydes using three types of catalysts:

(i) Dehydration catalysts such as alumina, silica-alumina, aluminum phosphate, or diammonium phosphate, at temperatures in excess of 350° C. *Kirk-Othmer Encyclopedia of Chemical Technology*, 3rd Ed., Vol. 2 (1978), New York, pp. 276–282 and *McGraw-Hill Encyclopedia of Science and Technology*, 5th Ed., Vol. 1 (1982), New York, p. 409. Specific examples include: $AlPO_4$ as disclosed in British Pat. No. 649,980;

(ii) Group VIII metals, such as nickel or cobalt, at temperatures of 170°–250° C., pressures of 1–20 atmospheres, and in the presence of hydrogen; Gardner et al U.S. Pat. No. 4,255,357 and Best U.S. Pat. No. 4,123,462;

(iii) Copper-based catalysts that are mixtures of copper with various oxides or alloys of copper and with Group VIII metals or compounds thereof. The range of process conditions disclosed in conjunction with these catalysts include a temperature range of 170°–270° C., and a pressure range of 1–150 atmospheres, hydrogen and non-hydrogen vapor, and liquid phase reactions are apparently also encompassed. There is some indication in the literature that these catalysts deactivate in the absence of hydrogen due to the formation of surface copper nitride, and that these catalysts have higher selectivity than catalysts referred to in paragraphs (i) and (ii) above. (Slaugh—U.S. Pat. No. 4,206,150; Habermann—U.S. Pat. No. 4,153,581; and Weigert—U.S. Pat. No. 4,254,061).

A palladium-based catalyst has been reported for phenol condensation with ammonia, but it is indicated to have limited activity and selectivity. Moreover, the alkylation of ammonia occurred only in the presence of hydrogen (Ono, Y, and Ishida, H., *Journal of Catalysis*, (1981), Volume 72, p. 121.

OBJECTIVES

The primary object of this invention is to provide a process for preparing higher substituted alkylamines from primary amines and alcohols with relatively higher selectivity or yield of specific products and/or at relatively lower temperatures and pressures as compared to prior art alkylation processes.

A further object of this invention is to provide specific catalyst systems whereby the foregoing selective reaction is effected under relatively mild reaction conditions.

BRIEF DESCRIPTION OF THE INVENTION

In accordance with the present invention, a primary alkyl amine and an alcohol of up to 12 carbon atoms are reacted at low temperature (50°–250° C.) over specific catalysts (alkali-treated catalysts generally or binary $Cu/ZnO$ and $Pd/SiO_2$ systems, with or without alkali treatment) to produce, with relatively good selectivity, secondary and tertiary alkylamines of the general formula, $R_1N(R_2)_2$, wherein $R_1$ is a lower alkyl or an aryl group, and $R_2$ is hydrogen or another lower alkyl or aryl group, with at least one of $R_2$'s being an alkyl or aryl group.

Exemplary of this process is the catalytic preparation of methyl-ethyl-amine under mild reaction conditions and from virtually stoichiometric reactant ratios of monomethyl amine and ethanol. Further, with the novel alkaline binary catalyst system disclosed herein, the shift co-reaction of by-product water and carbon monoxide is induced, so that hydrogen and carbon dioxide, which are more easily separated, are produced as final by-products.

The catalysts used in the present invention include alkali-treated alkylation catalysts generally, and copper-zinc oxide-based catalysts, and palladium (or platinum or iridium) supported catalysts, specifically. The alkali-treated or untreated copper-zinc oxide-based catalysts are also excellent catalysts for the shift reaction of by-products, and this catalyst system is therefore preferred.

One important aspect of the present invention is the discovery that certain catalysts, such as those comprising $Cu/ZnO$, $Cu/ZnO/K$, $Cu/ZnO/Rb$, $Cu/ZnO/Cs$, $Cu/ZnO/Al_2O_3$, $Cu/ZnO/Cr_2O_3$, $Cu/ZnO/ZnAl_2O_4$, $Pd/SiO_2$, $Pt/SiO_2$, $Ir/SiO_2$, $Ir/SiO_2$, Pd-Au alloy and Pd-Cu alloy, taught only in the prior art for methanol synthesis (primarily low temperature methanol synthesis), can catalyze the reaction of present interest at mild conditions, such as temperatures of 150°–250° C. and pressures of 1–100 atmospheres, in the absence of hydrogen and with good selectivity.

Another important aspect of this invention is the discovery that a key to better selectivity of the alkylation (minimizing disproportionation and scrambling of alkyl groups when making the secondary amines) is avoidance of residual acidity of the catalyst. This is accomplished by the introduction of a minor amount of alkali metal ion into the catalyst either during the catalyst synthesis or by their deposition upon the prepared catalyst. Localized acid sites are thus precluded, and this is applicable to conventional $Al_2O_3$ substrate catalysts, as well as the binary and Group VII catalysts which are a separate part of the present invention.

Spectroscopic study of the binary $Cu/ZnO$ catalyst prepared as taught herein indicates that this catalyst is a complex metal-oxide compound, in which the reduced copper (either in metallic or copper ionic form) is so finely divided as to appear amorphous under X-ray analysis. The finely divided copper particles may be dispersed, at least in part, within the crystalline structure of the zinc oxide. The alkali metal in the alkalized catalysts of this invention may be similarly dispersed or adsorbed on the surface of the finished catalyst, depending upon the manner of the introduction of the alkali ion into the system.

Among known catalysts disclosed herein, the highest selectivity for making secondary amines from alcohol and lower amines is displayed by Cu/ZnO catalysts that do not require $Cr_2O_3$, $Al_2O_3$, or $ZnAl_2O_4$ as a tertiary component.

According to the present invention, the primary (or secondary) amine reactant to alcohol ratio, expressed on a molar basis, can usefully range from 0.5:1 to about 20:1, but a range of 0.8:1 up to about 3:1 is preferred.

The Examples 1-9 that follow establish the following features:

(i) Alkylation of a primary amine by a primary alcohol occurs at fast rates and mild conditions, very selectively over the Cu/ZnO catalyst (Examples 1 and 7); also, with the Cu/ZnO/K, Cu/ZnO/Rb, and Cu/ZnO/Cs catalysts (Examples 10 and 11) but with poorer selectivity and concomitant disproportionation of the amine over the $Pd/SiO_2$ catalyst (Example 3);

(ii) Alkylation of a primary amine by a secondary alcohol occurs rapidly and at mild conditions, selectively over the Cu/ZnO catalyst (Example 2), and at a slower rate non-selectively with concomitant disproportionation of the amine over the $Pd/SiO_2$ catalyst (Example 4).

(iii) Disproportionation of the primary amine to the secondary amine and ammonia occurs, in the absence of alcohols. This side reaction occurs more quickly with the $Pd/SiO_2$ catalysts than with the Cu/ZnO catalysts (Example 5).

(iv) Disproportionation of the primary amine over the $Pd/SiO_2$ catalyst can be suppressed, relative to alkylation of the amine by alcohol, by lowering the temperature (Example 6).

(v) Hydrogen is not a necessary component of the reactants stream, nor does it retard the alkylation reaction over the Cu/ZnO catalysts (Examples 7 and 9).

(vi) Selectivity of the binary Cu/ZnO catalysts can be further increased by the addition of alkali metals to the catalysts (Examples 1, 10, and 11).

(vii) The overall activity of the presently disclosed $Pd/SiO_2$ catalyst (for the alkylation of isopropylamine with alcohols at 190° C. and 75 atm), is comparable with that of the amination of phenol over a $Pd/Al_2O_3$ catalyst at 200° C. and 1 atm, but the selectivity of the former is much greater than the latter (Examples 3 and 4).

The catalysts useful for the process of this invention may involve any composition of Cu/ZnO, but the most preferred compositions are in the weight % range of Cu/ZnO=30/70 to 67/33 wt%, the latter ratio being desirable where low surface area ($\approx 13$ m²/g) catalysts are needed.

In general, any $Cu/ZnO/M_xO_y$ where M is any metal ion generally appearing in oxide supports and x and y are dictated by the valence state of M may be improved, i.e., rendered more attrition-resistant for the alkylation reaction of this invention, by the incorporation in these catalysts of, or impregnation of the catalyst with, alkali metals, such as potassium, rubidium, and cesium.

However, the third component $M_xO_y$ is one that may lower (compared to the binary catalysts of this invention) the activity and/or the selectivity of amine alkylation by alcohols where a single hydrogen atom of the amine is replaced by the alkyl radical.

Furthermore, alkali-treated supported catalysts such as $Pd/M_xO_y$, $Pt/M_xO_y$, and $Ir/M_xO_y$ are also suitable. Also suitable are metallic alloys such as Cu-ZnO, Pd-Au, Pd-Cu, Pd-Ir, Pd-Ag and other combinations of these metals, which might or might not be supported on $M_xO_y$ materials.

In general, catalysts that promote the formation of alcohols from synthesis gas, or which dehydrogenate alcohols to aldehydes or ketones cleanly, are suitable for the process of this invention but at conditions at which alcohols are not typically produced, i.e., at the lower temperatures and pressures taught here.

The invention is further illustrated by the following examples:

EXAMPLE 1

A Cu/ZnO catalyst, of composition CuO/ZnO=30/70 weight %, was prepared by dissolving the metal nitrate salts in water heated to 80° C., coprecipitation of the metal hydroxycarbonates by the drop-wise addition of 1.0M $Na_2CO_3$ to the solution until the pH increased to 6.8, filtration, washing, and air-drying of the light blue solid, and calcination using a step-wise procedure to achieve a final temperature of 350° C. The dark material was pelletized from an aqueous slurry, sieved to 10-20 Mesh, and 2.45 g (2.9 ml) diluted with 7 ml of Pyrex beads was centered in the reactor. Reduction was carried out at 250° C. with a flowing 2% $H_2$/98% $N_2$ gas mixture until water was absent from the exit gas.

At ambient temperature, the reactor was pressurized to 75 atm with a $H_2/CO/CO_2$=70/24/6 vol % synthesis gas and the flow rate (GHSV) was adjusted to 5200 liters feed gas/liters catalyst/hour (1/1/hr). The reactor was heated to 225° C. to demonstrate that the catalyst was a typical methanol synthesis catalyst. There was 17.9% carbon monoxide conversion to methanol with a yield of 10.4 mol/l of catalyst/hr was observed.

The temperature was lowered to 190° C. (carbon conversion to methanol=2.0%, 1.1 mol methanol/l/hr). The synthesis gas was replaced by nitrogen flowing at the same gas hourly space velocity (0.612 mol $N_2$/hr). Under these experimental conditions, a 1:1 mole ratio mixture of ethanol and isopropylamine was pumped into the gas stream at the top of the reactor at the rate of 20 μl of liquid mixture per min. The product composition, exclusive of nitrogen, is presented in Table I. It is evident that approximately 35% of the isopropylamine was alkylated to ethylisopropylamine, with this reaction proceeding at the rate of 1.0 mol/l of catalyst/hr. The selectivity, defined as 100×(mol fraction of ethylisopropylamine)/(mol fractions of ammonia plus diethylamine plus ethylisopropylamine), was calculated as 88%, while no diethylisopropylamine was formed. (Table I)

TABLE I

The Results of the Reaction of Isopropylamine with Ethanol and a Pressure of 75 atm over Cu/ZnO Catalyst

| | Ethanol | Isoproply-amine[b] | Ammonia | Water | Isopropanol | Diethyl-amine | Ethylisopropyl-amine |
|---|---|---|---|---|---|---|---|
| mol/hr In | 0.0084 | 0.0084 | | | | | |

TABLE I-continued

The Results of the Reaction of Isopropylamine
with Ethanol and a Pressure of 75 atm over Cu/ZnO
Catalyst

| | Ethanol | Isoproply-amine[b] | Ammonia | Water | Isopropanol | Diethyl-amine | Ethylisopropyl-amine |
|---|---|---|---|---|---|---|---|
| mol/hr Out | 0.0057 | 0.0049 | 0.0003 | 0.0022 | 0.0006 | 0.0001 | 0.0029[a] |

[a] ± 0.0001 mol/hr
[b] total conversion to products = 41.7%, conversion to ethylisopropylamine = 34.5%

EXAMPLE 2

The selectivity to diisopropylamine is 100%, both at 190° C. and at 159° C. (Table II)

TABLE II

The Results of the Alkylation of Isopropylamine
With Isopropanol (and of the Disproportionation
of Isopropylamine at a Pressure of 75 atm over
Cu/ZnO Catalyst

| Temperature (°C.) | | Isopropanol | Isopropyl-amine | Ammonia | Water | Diisopropyl-amine |
|---|---|---|---|---|---|---|
| 190° C. | mol/hr In | 0.0086 | 0.0064 | | | |
| | mol/hr Out | 0.0046 | 0.0019[b] | 0.0000 | 0.0042 | 0.0043[a] |
| 190° C. | mol/hr In | | 0.0071 | | | |
| | mol/hr Out | | 0.0055 | 0.00073 | | 0.00086[a] |
| 159° C. | mol/hr In | 0.0083 | 0.0066 | | | |
| | mol/hr Out | 0.0048 | 0.0030[c] | 0.0000 | 0.0035 | 0.0037[a] |
| 159° C. | mol/hr In | | 0.0071 | | | |
| | mol/hr Out | 0.0069 | 0.0001 | | 0.0001 | |

[a] ± 0.0001 mol/hr
[b] total conversion = 70.3%
[c] total conversion = 54.5%

A 2.45 g (3.2 ml) portion of the CuO/ZnO (30:70) catalyst, prepared as described in Example 1, was placed in the reactor and reduced in the same manner. The reactor was pressurized to 75 atm with $H_2/CO/CO_2 = 70/24/6$ vol % synthesis gas, GHSV was set at 4700 1/1/hr, and the catalyst was tested at 250° C. A carbon conversion to methanol of 56% was observed, which is the expected catalytic activity.

The temperature was lowered to 190° C., and the synthesis gas was replaced by nitrogen at GHSV=4700 1/1/hr. An isopropylamine/isopropanol mixture with a 1.00:1.34 mole ratio was pumped into the gas stream at the rate of 20 µl of liquid mixture per min. About 70% of the isopropylamine was alkylated to diisopropylamine (1.35 mol/l/hr) and no evidence of disproportionation was observed, as indicated in Table II.

Isopropylamine by itself was pumped into the gas stream at 10 µl /min, and about 22% conversion to products by disproportionation was obtained. By decreasing the temperature to 159° C., the degree of disproportionation decreased to about 3% (Table II). Injecting a 1.00:1.26 mole ratio isopropylamine/isopropanol mixture at this temperature, at the rate of 20 µl/min, resulted in approximately 55% of the amine being converted to diisopropylamine by alkylation (1.16 mol/l of catalyst/hr). The amine conversion experiments were conducted during five days of continuous operation, and when removed from the reactor under nitrogen, the used catalyst was observed as pitch black. This color is an indication of the presence of highly interdispersed, electronically interacting catalyst components that produce the active state of the catalyst.

EXAMPLE 3

A 4.8 wt% Pd on $SiO_2$ catalyst was prepared by adding 200 g of 10-20 Mesh silica gel to 200 ml of concentrated hydrochloric acid containing 16.7 g of $PdCl_2$. The liquid was evaporated at 60° C. with the aid of evacuation, and the sample was dried under vacuum at 150° C. for 3 hr and then calcined in air at 400° C. for 4 hr. A portion of the catalyst was reduced in flowing hydrogen at 300° C. for 2 hr and at 500° C. for 2.5 hr. After cooling to room temperature, the reactor was pressurized to 75 atm with a $H_2/CO=70/30$ vol% synthesis gas. After calibrating the gas hourly space velocity to 1500 1/1/hr, the catalyst was heated to 250° C. and the methanol synthesis activity was determined for 53 hr, which was observed to be 3.0% conversion to methanol (0.55 mol/l/hr).

After decreasing the temperature to 190° C., the synthesis gas was replaced by nitrogen at the same GHSV, and these conditions were maintained for 44 hr. Injection into the nitrogen gas stream flowing at GHSV=1500 hr$^{-1}$ of a 1.45:1.00 mole ratio of an ethanol/isopropylamine mixture was carried out at the rate of 20 µl of liquid mixture per min. Approximately 73% of the isopropylamine was converted to products. Table III indicates that about equal quantities of ethylisopropylamine and diisopropylamine are formed, the yield of each being approximately 0.15 mol/l/hr. Lowering the temperature to 128° C. decreased the conversion to 0.2%, which occurred only by direct alkylation of the amine with ethanol with the product being ethylisopropylamine. The selectivity to ethylisopropylamine was 34.0%. (Table III)

TABLE III

The Results (mol %) of the Reaction of Isopropylamine with Ethanol at a Pressure of 75 atm over Pd/SiO$_2$ Catalyst

|  | Ethanol | Isoproply-amine[b] | Ammonia | Water | Isopropanol | Diethyl-amine | Ethylioso-propyla-mine | Diiso-propyl-amine |
|---|---|---|---|---|---|---|---|---|
| In | 0.0103 | 0.0071 | | | | | | |
| Out | 0.0086 | 0.0019 | 0.0012 | 0.0017 | 0.00080 | 0.00021 | 0.0015 | 0.0015 |

[a] ± 0.0001 mol/hr, except ± 0.0002 for water and diisopropylamine
[b] total conversion to products = 73.2%, conversion to ethylisopropylamine = 21.1%

EXAMPLE 4

A similar portion of the Pd/SiO$_2$ catalyst was treated as in Example 3 and equilibrated at 190° C. in flowing nitrogen. A 1.65:1.00 mole ratio isopropanol/isopropylamine mixture was pumped into the nitrogen gas stream flowing at GHSV=1500 hr$^{-1}$ at the rate of 20 μl of liquid mixture per minute. About 35% of the isopropylamine was converted to diisopropylamine at the rate of 0.2 mol/l/hr. Considering the yields of ammonia and water in Table IV, it is evident that approximately two-thirds of the amine product was formed by disproportionation and about one-third arose by alkylation of the amine with the alcohol. The selectivity of diisopropylamine was 60.6%. (Table IV)

TABLE IV

The Results of the Reaction of Isopropylamine With Isopropanol and a Pressure of 75 atm over Pd/SiO$_2$ Catalyst at 190° C.

|  | Isopro-panol | Isopropyl-amine[b] | Am-monia | Water | Diisopropyl-amine |
|---|---|---|---|---|---|
| mol/hr In | 0.0094 | 0.0057 | | | |
| mol/hr Out | 0.0085 | 0.0025 | 0.0013 | 0.00068 | 0.0020[a] |

[a] ± 0.0001 mol/hr
[b] total conversion to products = 56.1%; conversion to diisopropylamine = 35.1%

EXAMPLE 5

A 4.0 g (10 ml) portion of the Pd/SiO$_2$ catalyst was treated as in Example 3 and equilibrated at 190° C. in flowing nitrogen for 9 days. Isopropylamine was pumped into the nitrogen gas stream (GHSV=1500 hr$^{-1}$) at the rate of 10 μl/min (0.0071 mol/hr). About 50% of the isopropylamine was converted to the two products. The composition of the exit gas, exclusive of nitrogen, was isopropylamine/diisopropylamine/ammonia=47.2/25.0/27.8 mol%, which corresponds to a yield of diisopropylamine of 0.18 mol/l/hr. Decreasing the temperature to 159° C. produced at exit gas composition, exclusive of nitrogen, of isopropylamine/diisopropylamine/ammonia=95.2/2.5/2.3 mol%, and a yield of the disproportionation product of 0.02 mol/l/hr. (Table V)

EXAMPLE 6

A similar portion of the Pd/SiO$_2$ catalyst was treated as in Example 3 and equilibrated at 190° C. in flowing nitrogen (GHSV=1500 hr$^{-1}$) for 36 hr. After lowering the temperature to 159° C., a 1.1:1.0 mole ratio isopropanol/isopropylamine mixture was pumped into the gas stream at the rate of 20 μl of liquid mixture per min. As indicated in Table V, approximately 7% of the isopropylamine was converted to diisopropylamine (at a rate of 0.5 mol/l/hr), and most of the conversion was accomplished by alkylation rather than by disproportionation.

In comparison with Example 4, it is demonstrated that lower temperature inhibits the disproportionation of isopropylamine over this Pd-based catalyst. However, Example 2 shows that the Cu/ZnO catalyst is appreciably more active for the alkylation of isopropylamine with isopropanol. The selectivity of diisopropylamine was 76.7%. (Table V)

TABLE V

The Results of the Reaction of Isopropylamine With Isopropanol and a Pressure of 75 atm over Pd/SiO$_2$ Catalyst at 159° C.

|  | Isopro-panol | Isopropyl-amine[b] | Am-monia | Water | Diisopropyl-amine |
|---|---|---|---|---|---|
| mol/hr In | 0.0079 | 0.0071 | | | |
| mol/hr Out | 0.0076 | 0.0066 | 0.00014 | 0.00033 | 0.00046[a] |

[a] ± 0.0001 mol/hr
[b] total conversion to products = 7.0%; conversion to diisopropylamine = 5.6%

EXAMPLE 7

After purging, the reactor was pressurized to 26 atm with CH$_3$NH$_2$/N$_2$=3/97 mol%, GHSV was set at 8870 hr$^{-1}$, and the Cu/ZnO catalyst was tested at 190° C. 1-Butanol was injected into the gas stream at the rate of 25 μl/min. (2:1 mole ratio). Approximately 52.4 mol% of 1-butanol was converted to 1-butyl N-methyl amine (methyl N-butylamine) with the selectivity of 95.5% to this amine, the side product being di-1-butyl N-methylamine. (Table VI)

TABLE VI

The Results of the Reaction of Methylamine With 1-Butanol at 26 atm

|  | CH$_3$NH$_2$ | H$_2$O | 1-BuOH | BuNHCH$_3$ | Bu$_2$NCH$_3$ |
|---|---|---|---|---|---|
| mol/hr In | 0.0326 | 0.0000 | 0.0164 | 0.0000 | 0.0000 |
| mol/hr Out | 0.0236 | 0.0094 | 0.0070 | 0.0086[a] | 0.0004 |

[a] 0.0002 mol/hr

EXAMPLE 8

The reactor was pressurized to 24 atm with CH$_3$NH$_2$/N$_2$=3/97 mol%. GHSV was set at 7360 hr$^{-1}$ and the Cu/ZnO catalyst was equilibrated at 190° C. 1-Butanol was pumped at 25 μl/min. (1.7:1.0 mole ratio). About 50% of 1-butanol was converted to 1-butyl N-methylamine with the selectivity of 96.5% to this amine, the side product being di-1-butyl N-methylamine. (Table VII)

TABLE VII

The Results of the Reaction of Methylamine With 1-Butanol at 24 atm

|  | CH$_3$NH$_2$ | H$_2$O | 1-BuOH | BuNHCH$_3$ | Bu$_2$NCH$_3$ |
|---|---|---|---|---|---|
| mol/hr In | 0.0271 | 0.0000 | 0.0164 | 0.0000 | 0.0000 |
| mol/hr Out | 0.0187 | 0.0088 | 0.0076 | 0.0082[a] | 0.0003 |

TABLE VII-continued

| The Results of the Reaction of Methylamine With 1-Butanol at 24 atm | | | | | |
|---|---|---|---|---|---|
| | $CH_3NH_2$ | $H_2O$ | 1-BuOH | $BuNHCH_3$ | $Bu_2NCH_3$ |
| Out | | | | | |

$^a$ ± 0.0002 mol/hr

EXAMPLE 9

The reactor was pressurized to 30 atm with $H_2CH_3NH_2/N_2=21.36/2.36/76.28$, mol%, GHSV was set at 9360 hr$^{-1}$ and the catalyst was tested at 190° C. 1-Butanol was pumped at 25 μl/min. (1.7:1.0 mole ratio). About 56% of the 1-Butanol was converted to 1-butyl N-methylamine with the selectivity of 95.8% to this amine, the side product being di-1-butyl N-methylamine. (Table VIII)

TABLE VIII

| The Results of the Reaction of Methylamine With 1-Butanol at 30 atm in the Presence of Hydrogen | | | | | |
|---|---|---|---|---|---|
| | $CH_3NH_2$ | $H_2O$ | 1-BuOH | $BuNHCH_3$ | $Bu_2NCH_3$ |
| mol/hr In | 0.0271 | 0.0000 | 0.0164 | 0.0000 | 0.0000 |
| mol/hr Out | 0.0178 | 0.0099 | 0.0062 | 0.0092$^a$ | 0.0004 |

$^a$ ± 0.0002 mol/hr

EXAMPLE 10

A more attrition-resistance catalyst containing potassium was prepared that also exhibited high selectivities in the alkylation of amines. A 3.00 g portion of the Cu/ZnO=30/70 mol% catalyst, prepared as described in Example 1, was placed in the reactor and reduced in the same manner. The catalyst was removed from the reactor under a nitrogen atmosphere and was added to 25 ml of a nitrogen-purged, aqueous solution containing 0.009 g of KOH at 50° C. The solution was evaporated to dryness under a flowing nitrogen atmosphere. A 2.45 g (3.0 ml) portion of the dried catalyst, which contained 0.52 mol% K on the basis of metal content, was placed in the reactor. The reactor was pressurized to 75 atm with nitrogen, GHSV was set to 5000 hr$^{-1}$, and the catalyst was equilibrated at 190° C. A 1:1 mole ratio ethanol/isopropylamine mixture was injected into the gas stream at the rate of 20 μl of liquid mixture per min. About 17% of the isopropylamine was converted to ethylisopropylamine at the rate of 0.47 mol/l catalyst/hr, as deduced from Table IX. No diethylisopropylamine was detected in the exit gas. (Table IX)

TABLE IX

| The Results of the Reaction of Isopropylamine with Ethanol over K/Cu/ZnO Catalyst | | | | | | |
|---|---|---|---|---|---|---|
| | Ethanol | Isoproplyamine | Ammonia | Water | Isopropanol | Ethylisopropylamine |
| mol/hr In | 0.0084 | 0.0084 | | | | |
| mol/hr Out | 0.0072 | 0.0065 | 0.0003 | 0.0010 | 0.0003 | 0.0014$^a$ |

$^a$ ± 0.0001 mol/hr

EXAMPLE 11

A more attrition-resistant catalyst containing rubidium was prepared that exhibited high selectivities in the alkylation of amines. A 3.00 g portion of the Cu/ZnO=30/70 mol% catalyst, prepared as described in Example 1, was placed in the reactor and reduced in the same way. The catalyst was removed from the reactor under a nitrogen atmosphere and was added to 10 ml of a nitrogen-purged, aqueous solution containing 0.0167 g of RbOH at 50° C. The solution was evaporated to dryness under a flowing nitrogen atmosphere. A 2.45 g (3.0 ml) portion of the dry catalyst, which contained 0.54 mol% Rb on the basis of metal content, was placed in the reactor. The reactor was pressurized to 75 atm with nitrogen, GHSV was set to 5000 hr$^{-1}$, and the catalyst was equilibrated at 190° C. A 1:1 mole ratio ethanol/isopropylamine mixture was injected into the gas stream at the rate of 20 μl of liquid mixture per min. Approximately 23% of the isopropylamine was converted to ethylisopropylamine at the rate of 0.63 mol/l catalyst/hr, as demonstrated in Table X. No diethylisopropylamine was detected in the exit gas.

TABLE X

| The Results of the Reaction of Isopropylamine with Ethanol over Rb/Cu/ZnO Catalyst | | | | | | |
|---|---|---|---|---|---|---|
| | Ethanol | Isoproplyamine | Ammonia | Water | Isopropanol | Ethylisopropylamine |
| mol/hr In | 0.0084 | 0.0084 | | | | |
| mol/hr Out | 0.0063 | 0.0061 | 0.0005 | 0.0015 | 0.0005 | 0.0019$^a$ |

$^a$ ± 0.0003 mol/hr

While this invention has been described with reference to specific embodiments thereof, it is not considered to be limited thereto. Accordingly, the appended claims are intended to be construed to encompass not only those forms and embodiments of the invention specifically described or generally referred to herein but to such other embodiments and forms of the invention as may be devised by those skilled in the art without departing from the true spirit and scope of the present invention.

We claim:

1. A selective alkylation process for preparing higher substituted amines by reacting a primary amine with a straight or branched chain alcohol having up to twelve carbon atoms under mild reaction conditions, comprising one to 100 atmospheres and 50° to 250° C., wherein the amine to alcohol reactant ratio, expressed on a molar basis, ranges from approximately 0.5:1 to about 20:1, in the presence of a catalyst system selected from the group consisting of (a) a binary combination of essentially amorphous finely divided metallic copper dispersed in zinc oxide and (b) a deacidified copper or palladium combination with at least one additional metal oxide compound selected from the group of zinc oxide, alumina, and chromium oxide.

2. The process of claim 1, wherein said deacidified copper or palladium is the product of a process wherein said catalyst system is de-acidified by treatment with potassium, rubidium, or cesium.

3. The process of claim 1, wherein said binary catayst includes from 2 to about 70 mole percent copper and from 30 to 98 mole percent zinc oxide.

4. The process of claim 1, wherein said reactant amine to alcohol ratio ranges from 0.8:1 to about 3:1.

5. The process of claim 1, wherein said palladium catalyst is supported on silica with said palladium comprising from 2 to 8 weight percent of the total catalyst and the silica comprises from 92 to 98 weight percent of the total catalyst.

6. The process of claim 1, wherein said binary catalyst comprises 30 to 67 mole percent copper and 70 to 33 mole percent zinc oxide.

7. The process of claim 2, wherein the catalyst treatment process results in a catalyst system with potassium, rubidium, or cesium deposited in the surfaces of said catalyst and said potassium, rubidium, and cesium comprise 0.2-2 weight percent of said total catalyst system.

8. The process of claim 1, wherein the reaction is carried out in the presence of nitrogen gas.

9. An improved alkylation process for preparing higher substituted amines by reacting a primary or secondary amine with a straight or branched chain alcohol having up to 12 carbon atoms under mild reaction conditions, comprising 1 to 100 atmospheres and 50° to 250° C., wherein the amine to alcohol reaction ratio, expressed on a molar basis, ranges from 0.5:1 to 20:1, in the presence of a catalyst system selected from one of an alkaline, binary, or tertiary alkylation catalyst consisting essentially of metallic copper dispersed in zinc oxide, copper dispersed in zinc oxide, copper dispersed in zinc oxide and alumina, copper dispersed in zinc oxide and chromium oxide, copper dispersed in zinc oxide and zinc aluminum oxide, or palladium, platinum, or iridium metals supported on an oxidic compound selected from the group of silicon dioxide, zinc oxide, alumina, and chromium oxide or on a second metallic component selected from the group of copper, silver, gold, iridium and platinum.

* * * * *